United States Patent [19]

Janin

[11] 3,936,356
[45] Feb. 3, 1976

[54] PROFILE RECOGNITION METHOD AND APPARATUS FOR IDENTIFYING BACTERIA

[75] Inventor: Pierre R. Janin, New York, N.Y.

[73] Assignee: Analytab Products Inc., Plainview, N.Y.

[22] Filed: Mar. 21, 1974

[21] Appl. No.: 453,434

Related U.S. Application Data

[63] Continuation-in-part of Ser. No. 349,698, April 10, 1973, abandoned.

[52] U.S. Cl. .......................... 195/103.5 R; 195/127
[51] Int. Cl.² ........................................... C12K 1/04
[58] Field of Search .............. 195/103.5 R, 127, 139

[56] References Cited
UNITED STATES PATENTS 3,810,739   5/1974   Nussbaum ................ 195/103.5 R X

*Primary Examiner*—Lionel M. Shapiro
*Assistant Examiner*—Robert J. Warden
*Attorney, Agent, or Firm*—Kenyon & Kenyon Reilly Carr & Chapin

[57] ABSTRACT

A suspension of an unknown micro-organism is introduced into a plurality of reaction chambers, each containing a different specific biochemical reagent. The presence or absence of each reaction is subsequently transformed to a multi-digit numerical profile, which serves to identify the micro-organism by means of a numerical Profile Register. Apparatus is also provided to facilitate the transformation of the test result data to the numerical profile while simultaneously providing a verification of the transformation.

23 Claims, 12 Drawing Figures

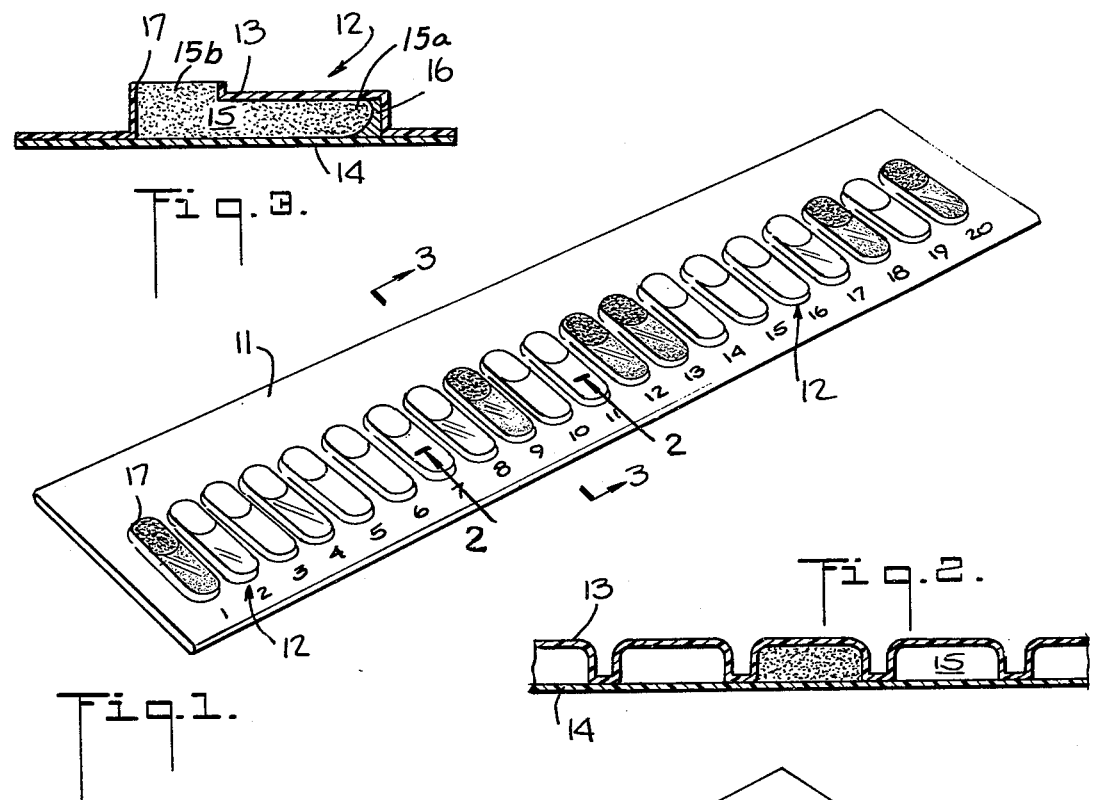
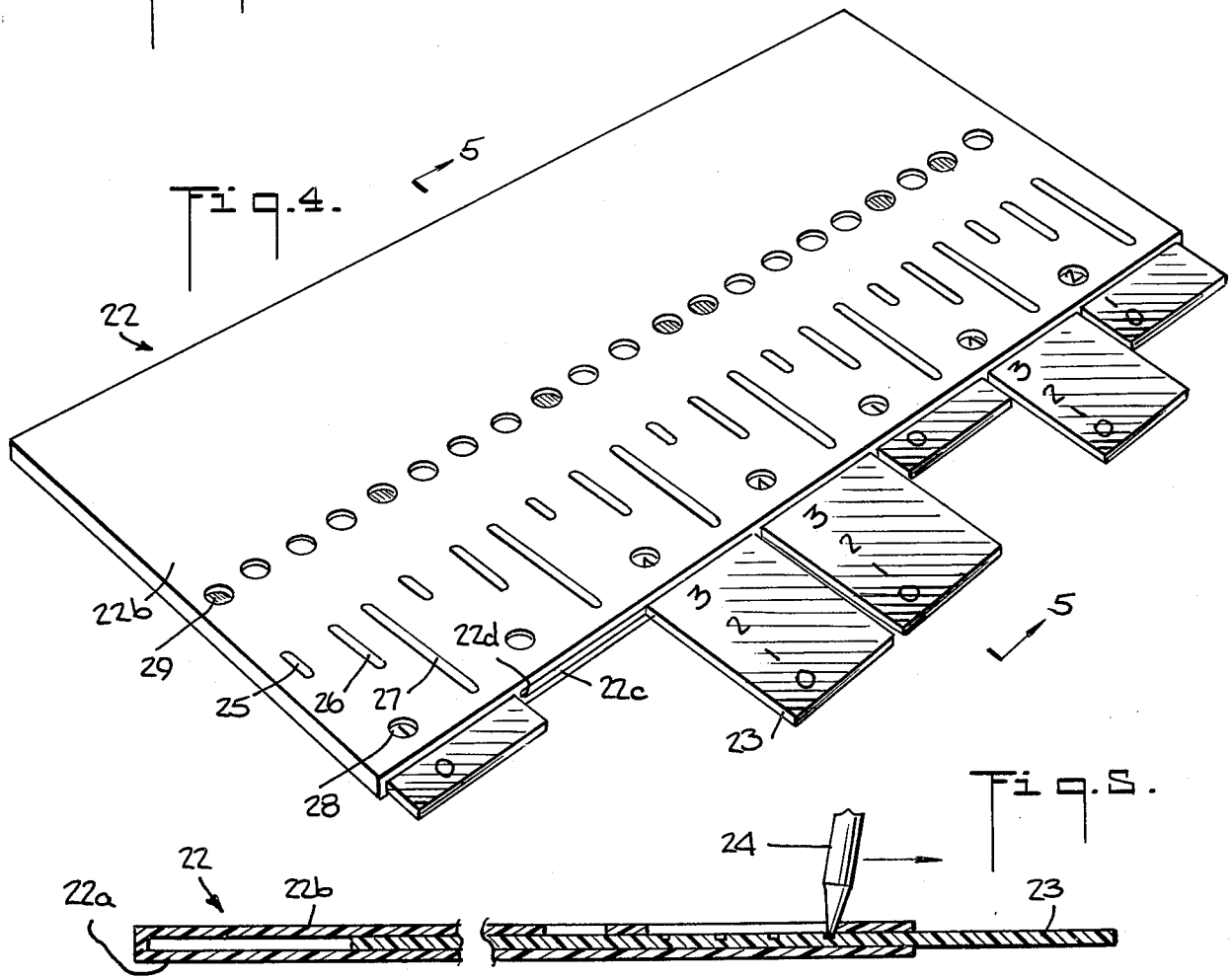

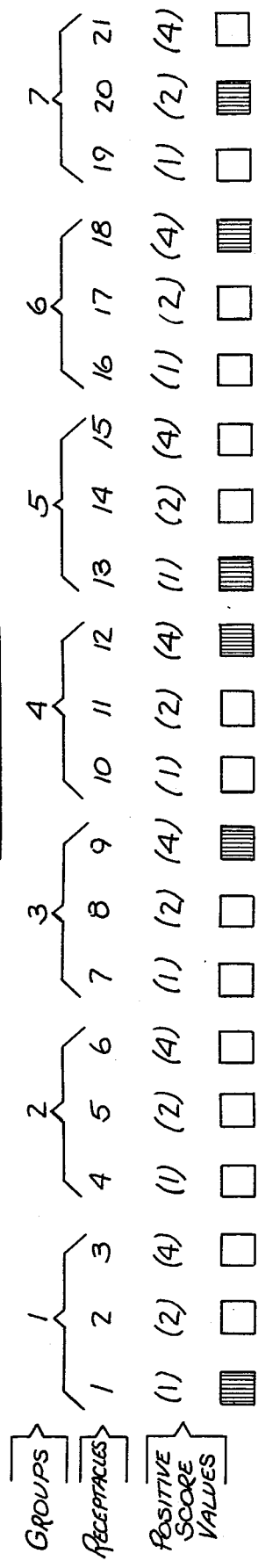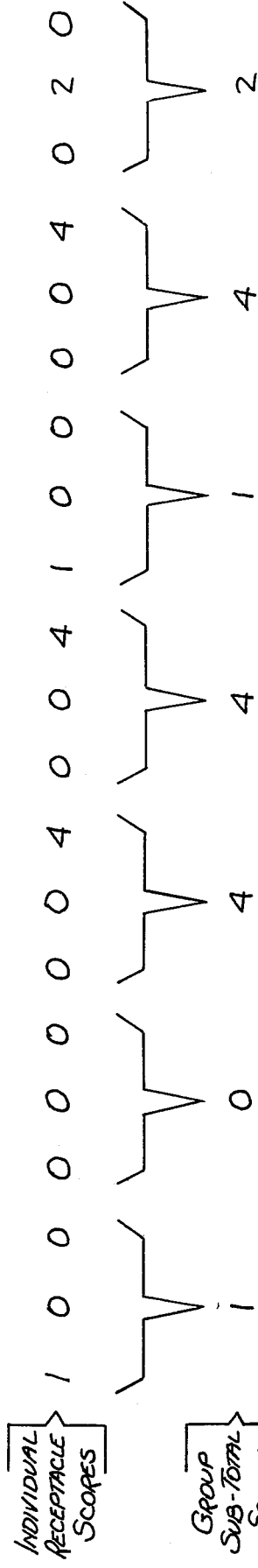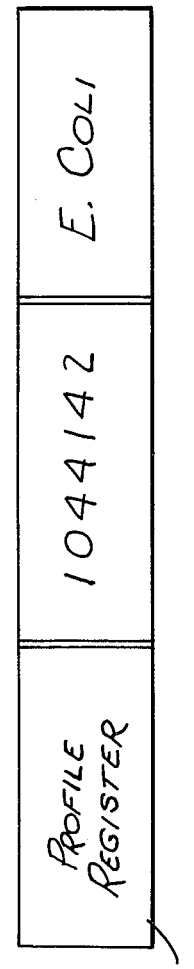
Fig. 2.

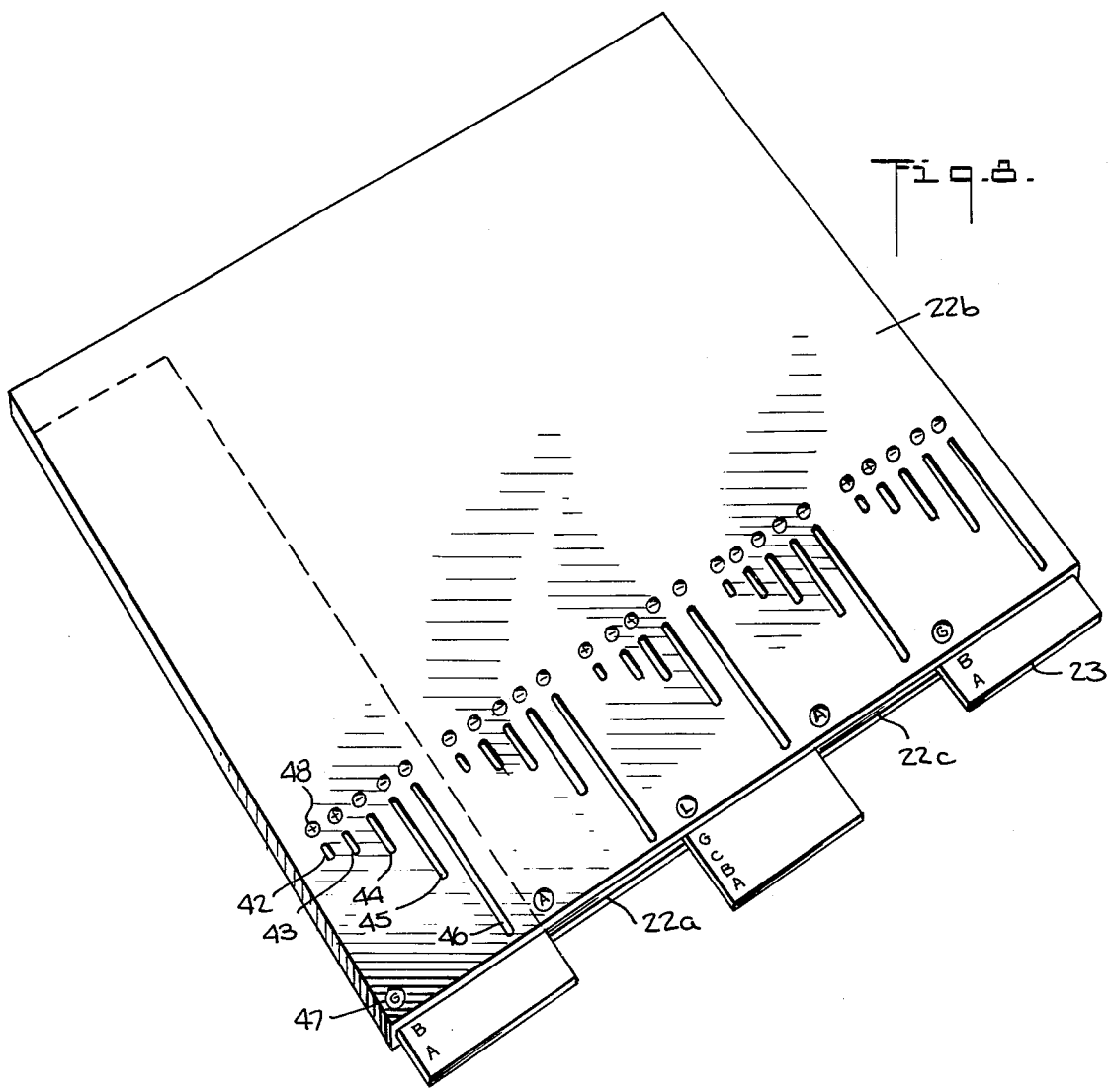

Fig.9.

| | | | | | |
|---|---|---|---|---|---|
| | + | + | + | + | + | 49
| | − | + | + | + | + |
| | + | − | + | + | + |
| | − | − | + | + | + |
| | + | + | − | + | + |
| | − | + | − | + | + |
| | + | − | − | + | + |
| | − | − | − | + | + |
| | + | + | + | − | + |
| | − | + | + | − | + |
| | + | − | + | − | + |
| | − | − | + | − | + |
| | + | + | − | − | + |
| | − | + | − | − | + |
| | + | − | − | − | + |
| | − | − | − | − | + |
| 9 | + | + | + | + | − |
| 8 | − | + | + | + | − |
| 7 | + | − | + | + | − |
| 3 | − | − | + | + | − |
| 6 | + | + | − | + | − |
| X | − | + | − | + | − |
| 2 | + | − | − | + | − |
| K | − | − | − | + | − |
| 5 | + | + | + | − | − |
| 0 | − | + | + | − | − |
| W | + | − | + | − | − |
| N | − | − | + | − | − |
| Z | + | + | − | − | − |
| Q | − | + | − | − | − |
| R | + | − | − | − | − |
| F | ⊖ | ⊖ | ⊖ | ⊖ | ⊖ |
| 4 | | | | | |
| S | | | | | |
| T | | | | | |
| J | | | | | |
| U | | | | | |
| M | | | | | |
| P | | | | | |
| E | | | | | |
| Y | | | | | |
| H | | | | | |
| L | | | | | |
| D | | | | | |
| G | | | | | |
| C | | | | | |
| B | | | | | |
| Ⓐ | | | | | |

23

41

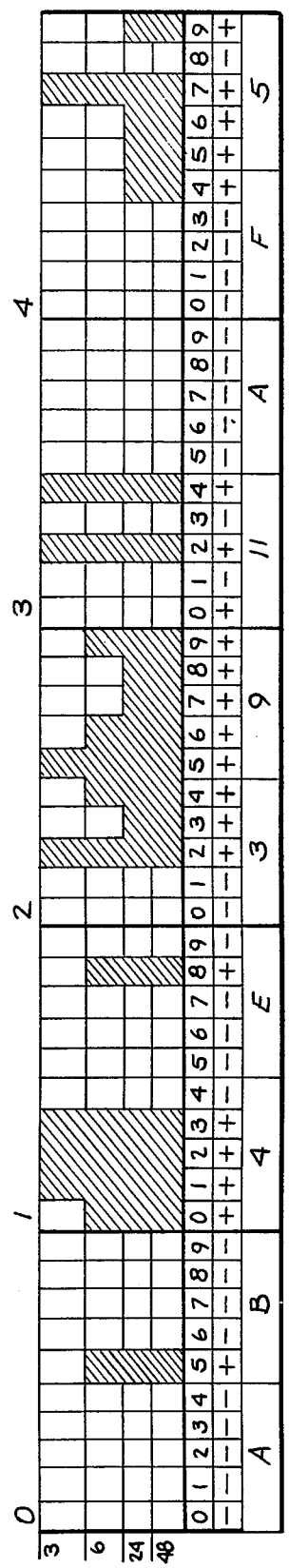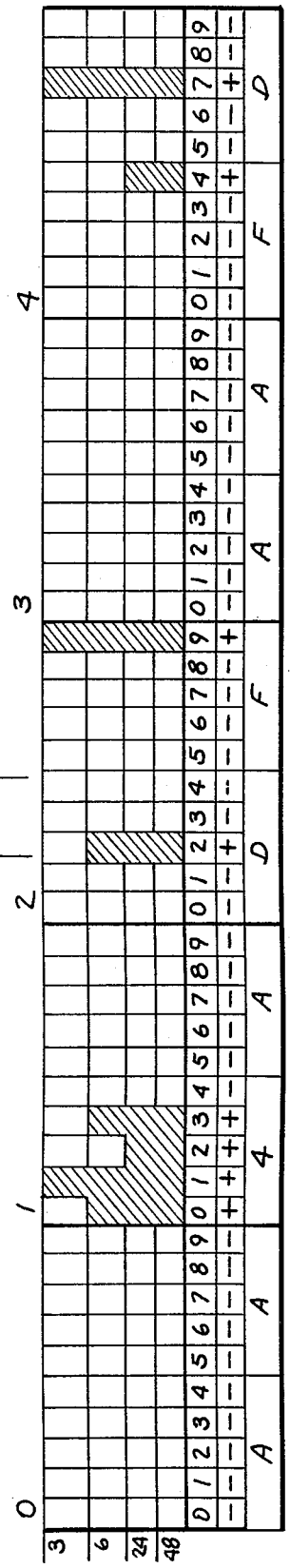

PROFILE RECOGNITION METHOD AND APPARATUS FOR IDENTIFYING BACTERIA

This is a continuation-in-part of application Ser. No. 349,698, filed Apr. 10, 1973, now abandoned.

BACKGROUND OF THE INVENTION

This invention relates to the identification of unknown bacteria by means of simultaneously performed biochemical reactions. More particularly it relates to a unique method for transforming the results of the biochemical reactions into a numerical profile representative of the bacterium being tested and subsequently consulting a Profile Register to obtain the identification.

A mechanical coder is provided which enables the user to efficiently transform the above-stated results to the numerical profile. This mechanical coder may also be provided with a color check feature to enable the user to visually verify his results.

The identification of bacteria is based on several characteristics of these organisms: reaction to certain biochemicals, serological behavior, lysotyping, bacteriophage, morphology, physiology, cell arrangement, etc.

In the routine clinical laboratory, the biochemical reactions form the primary basis for classification at the level of the tribe and the genus within the family Enterobacteriaceae. The behavior of bacterial organisms with particular biochemicals has been reported by several investigators. See, e.g., Edwards, P. R. and Ewing, W. H. *Identification of Enterobacteriaceae*. Third edition. Burgess Publishing Company, Minneapolis, Minnesota., 1972; Le Minor, L. *Le diagnostic de laboratoire des bacilles a gram negatifs Enterobacteries*. Tome 1, 4$^e$ edition, 1972. Editions de la Tourelle, St. Mande - 94, France; Cowan, S. T. and Steel, K. J. *Manual for the Identification of medical bacteria*. Cambridge at the University Press, 1970; Kauffman, F. *The bacteriology of Enterobacteriaceae*. Second edition, 1969. The Williams and Wilkins Company, Baltimore, Maryland.

Some of these reactions are clear-cut, being mostly positive or negative, whereas some others are variable. Based on a large number of organisms, percentages of positive or negative reactions have been established and reported. Several schema to interpret the results of biochemical reactions have been developed.

Because of the complexity of the interpretation of the data obtained, a sequential method of dichotomous keys, presented in the form of flow diagrams, is presently widely used. These flow diagrams base the selection of each succeeding biochemical test on the results of the previous one. This approach, even though practical in routine, is a simplification which, in the case of less common biotypes, can lead to misidentification.

The possible application of computer technology in the clinical laboratory has allowed a new approach toward the identification of an organism in testing it simultaneously with a large number of biochemicals. The computer memory can store probability of occurrence for each biochemical and, when matched with an unknown, the computer can provide a diagnosis based on probability. Minimum level of probability can establish the acceptability of the answer provided. This approach requires a huge memory which imposes the use of a computer and has the setback of describing combinations of reactions which are mathematically possible, but never encountered in organisms.

The Profile Recognition Method of this invention also tests the organisms simultaneously with a large number of biochemical characters, but only describes combinations which are most probably to occur with actual organisms. For example, for twenty biochemical reactions, the computer would allow 1,048,576 combinations. On the other hand traditional flow diagram techniques would only provide less than one hundred combinations. The Profile Recognition Method of the invention provides about 1500 combinations which is a more realistic number of combinations considering the probable number of biotypes.

The method of this invention enables the user to convert the results of the biochemical tests into a Profile Recognition Number, which is utilized to identify the bacterium by consulting a Profile Register. Methods are provided in the Profile Register to account for rare strains of bacteria as well as to aid in correcting errors in interpreting the biochemical test results made by the user.

The identification process can be further simplified by use of a coder to generate the Profile Recognition Number. This enhances the speed of identification.

Errors in transforming the biochemical test results into the Profile Recognition Number may be made by the user. To reduce these errors, the coder may also be provided with a color-check feature, whereby the user can visually compare the colors produced in the reaction chambers with a set of colors generated on the coder corresponding to the indicated Profile Recognition Number.

As used herein, the terms "numerical profile," "Profile Recognition Number," "number" and "digit" are understood to include both numerical and alphanumerical representations.

SUMMARY OF THE INVENTION

The Profile Recognition Method of this invention tests the micro-organism simultaneously with a large number of biochemical characters, attributing to each of them the same weight. The Profile Recognition Method not only considers each character, but also the probability of simultaneous occurrence or mutual exclusion of biochemical characters. This method has long been advocated by taxonomists.

This classification of micro-organisms such as bacteria, on the basis of overall similarities, has also long been advocated by microbiologists. Yet, it has not found a wide acceptance in the routine clinical laboratory because of the work involved in performing a large number of biochemical reactions simultaneously and because of the complexity to interpret the results gathered. The method of this invention allows the very accurate performance of a large number of biochemical tests with convenience, speed and economy.

The system allows standardization of the technique. The Profile Recognition Method will now allow consistency of the interpretation. This method will increase further the confidence of the technologist in an accurate identification and a shorter reporting time to the clinicians for better patient therapy.

It is an object of this invention to provide a simple, fast, efficient and economical method for identification of bacteria. It is a further objection to provide a more errorproof method for said identification.

It is still a further object to provide a more consistent method for recognition of bacteria.

It is also an object to provide a simple and convenient coder for mechanically aiding said identification.

It is still a further objection of this invention to provide a means to check on the accuracy of the identification.

Further objects will become apparent from the detailed specification.

BRIEF DESCRIPTION OF THE DRAWINGS

FIG. 1 is a perspective view of a biochemical test strip of twenty individual reaction chambers.

FIG. 2 is a perspective view of a representative section of the test strip along the long axis of each chamber.

FIG. 3 is an enlarged vertical section view of an individual reaction chamber taken along the line 3—3 in FIG. 1.

FIG. 4 is a perspective view of a preferred form of the coder device.

FIG. 5 is a vertical section view of the coder device taken along the line 5—5 in FIG. 4.

FIG. 7 is a representation of the steps of the method of the invention.

FIG. 8 is a perspective view of another coder device.

FIG. 9 is an illustration of one indicator slide for the coder device of FIG. 8.

FIG. 10 is a representation of the time variation chart of this invention.

FIGS. 11A and 11B are representations of a time variation chart which includes the score values, the intermediate values and the final values of this invention.

DESCRIPTION OF THE PREFERRED EMBODIMENTS

Figure 6:
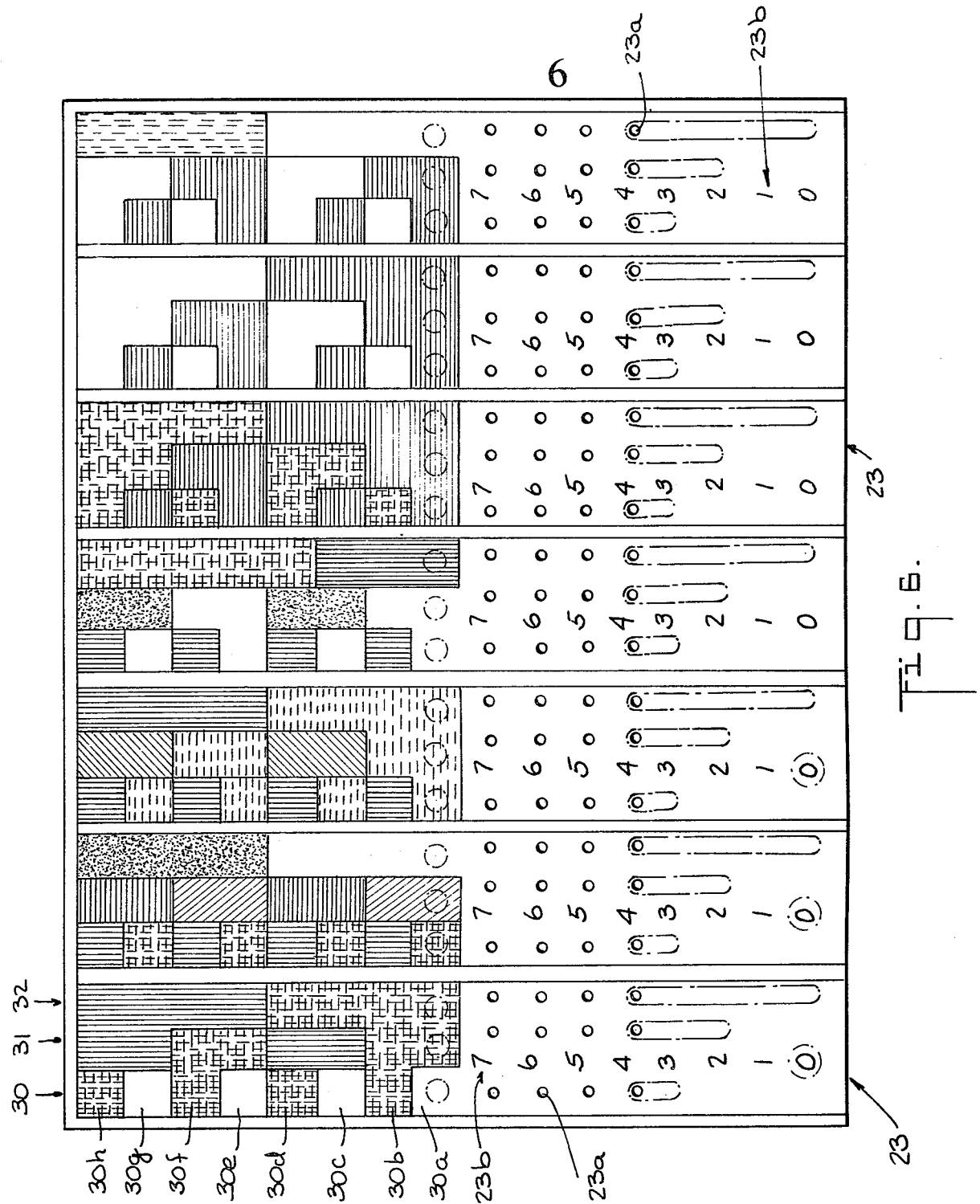
FIG. 6 is an illustration of the seven indicator slides for the preferred form of the coder device.

The invention relates to a simple and efficient method for the identification of micro-organisms including bacteria. The method generally comprises the steps of culturing and isolating the unknown bacterium on a selective medium, reacting small portions of the culture with preselected biochemical test reagents, transforming the results of these biochemical tests into a numerical profile, and then consulting a tabulated list such as a catalog or register of numerical profiles (Profile Register) to identify the bacterium.

The unknown bacterium may be cultured by any convenient standard method and in the usual nutrient broths. The culturing should be done for a sufficient time to produce a reasonable concentration of bacteria in the culturing medium. The reliability of the biochemical tests will be increased by allowing the medium to culture for a longer period of time.

After the desired culturing period, an individual colony is suspended in about 2 to 5 milliliters of an appropriate diluent, which may or may not contain a nutrient. This bacterial suspension is then transferred in micro-quantities to the reaction chambers by any suitable means, such as a Pasteur pipette.

While the biochemical test reactions can be carried out in any convenient equipment and by any convenient method, it is preferably to carry out the test reactions in a special plate manufactured for the purpose. One such test plate is manufactured by Analytab Products, Inc. of Carle Place, Long Island, New York.

As shown in FIG. 1, the test plate 11 comprises a plurality of small identified reaction chambers 12 (identified by numbers for example) disposed linearly along the strip. As shown in FIG. 2, the strip is conveniently formed attaching two molded plastic strips 13 and 14 so as to form individual compartments 15. FIG. 3 illustrates the configuration of each reaction chamber.

As supplied by the manufacturer, there is a measured quantity of test reagent 16 and possible nutrients situated in the closed end of each reaction chamber. It is most convenient if the reagent mixture therein is in solid form (dehydrated), as then the test plates may be more easily stored and handled. As some of the reagent mixtures tend to be slightly unstable, it is preferable to keep the unused test plates refrigerated until ready for use.

Referring again to FIG. 1, each test plate 11 contains a plurality of micro-reaction chambers 12. Each micro-reaction chamber along the plate has a different predetermined reaction mixture contained therein. Thus each biochemical test can be performed simultaneously. The test plates can be supplied with differing numbers of tests. Rapid identification has been done with a series of ten tests and more accurate ones have been performed using a series of twenty tests and even fifty tests.

The sequence of twenty micro-tests for enterobacteriaceae has been about 88% accurate, and reaches about 93% when using a more concentrated liquid culture. See, Washington, J. A. et al, *Evaluation of Accuracy of Multitest Micromethod System for Identification of Enterobacteriaceae*, Applied Microbiology, 22:267–9 (Sept. 1971) A later investigator obtained 96.4% accuracy. Smith, P. B. et al, *API System: a Multitube Micromethod for Identification of Enterobacteriaceae*, Applied Microbiology, 24:449–52 (Sept. 1972)

TWENTY TEST METHOD

While any of these or other numbers of tests may be used with the method of this invention, it has been found to be preferable to utilize a series of twenty tests. The following description will illustrate the use of one twenty-test method for the identification of enterobacteriaceae, but it is important to realize that it is for purposes of illustration only and may be adapted to any number of tests.

The twenty tests selected are:
1. B-galactosidase (ONPG)
2. arginine dihydrolase (ADH)
3. lysine decarboxylase (LDC)
4. ornithine decarboxylase (ODC)
5. citrate (CIT)
6. $H_2S$
7. urease (URE)
8. tryptophane deaminase (TDA)
9. indole (IND)
10. acetoin (VP)
11. gelatin (GEL)

and fermentation tests of 12. glucose (GLU)
13. mannitol (MAN)
14. inositol (INO)
15. sorbitol (SOR)
16. rhamnose (RHA)
17. saccharose (SAC)
18. melibiose (MEL)
19. amygdaline (AMY)
20. arabinose (ARA)

Commercially available test strips containing the reagents and nutrients necessary to perform the above twenty biochemical tests are available from Analytab Products, Inc., Carle Place Long Island, New York, referred to as the API Enteric System.

Also available from Analytab Products, Inc. are test strips containing materials to conduct only ten of the above biochemical tests. These ten biochemical tests can provide quick test results with some sacrifice of accuracy compared to the twenty-test method.

For anaerobic bacteria, a similar set of twenty biochemical tests is available. The following list represents the specific biochemical tests which are provided for in the available strips:

1. Indole
2. Urea
3. Glycerol
4. L (+) arabinose
5. D (+) xylose
6. Glucose
7. Mannose
8. Rhamnose
9. Mannitol
10. Sorbitol
11. Gelatine
12. Esculine
13. Salicine
14. Cellobiose
15. Maltose
16. Lactose
17. Saccharose
18. Trehalose
19. Melezitose
20. Raffinose The above three sets of available test strips are meant to be representative only. Other sets of biochemical, chemical enzymatic, etc., tests can be utilized. The number of tests in the set is not critical, but should be of sufficient number to produce reasonable accuracy.

The order of tests on the test strip is of no consequence as all tests are performed simultaneously and are given equal weighting for the final identification. While the ordering of tests on the test strip is immaterial, once an order is selected, it is important to consistently use this same order. In each case, the Profile Register will depend on the ordering of tests on the strip.

The description of the methods of this invention below will be illustrated by using the API Enteric System of Analytab Products, Inc. This is meant to be illustrative only and the methods of this invention are equally applicable to any set of biochemical tests.

Referring again to FIG. 3, each reaction chamber 12 is filled with the bacterial suspension using the open end 17 of each reaction chamber 12. No attempt is made to agitate or otherwise distribute the contents. The entire test plate 12 is then placed into an incubation chamber and allowed to incubate for about 18 to 24 hours at a temperature range of about 35° to 40°C. The incubation chamber can be close-fitting with the test plate and may contain water, thereby reducing evaporation from the reaction chambers.

When the test strip for anaerobic bacteria is used, provision is made in the incubation chamber (not shown) to replace the air contained therein with a suitable non-oxidizing atmosphere. Thus the test strip is placed into the special incubation chamber, the chamber sealed, the air replaced by a non-oxidizing gas and the test performed. In this case, the incubation chamber is preferably manufactured from a transparent material in order to facilitate the checking of reaction results without introducing air into the system.

For each test, the presence or absence of a reaction is detected. In the chart for enterobacteriaceae below, positive means that a reaction has taken place in the numbered test chamber and negative means the absence of any reaction.

By merely checking the color, except for test 11 where the presence or absence of diffusion constitutes the test, the user can easily determine those tests giving a positive result and those giving a negative result.

| | TEST | POSITIVE | NEGATIVE |
|---|---|---|---|
| 1. | ONPG (Lactose) | Yellow | Clear |
| 2. | Arginine | Red | Yellow |
| 3. | Lysine | Red | Yellow |
| 4. | Ornithine | Red | Yellow |
| 5. | Citrate | Blue | Green |
| 6. | $H_2S$ | Black | Clear |
| 7. | Urea | Red | Yellow |
| 8. | Tryptophane | Brown | Yellow |
| 9. | Indole | Red | Yellow |
| 10. | Voges-Proskauer | Red | Clear-Pink |
| 11. | Gelatin | diffusion | no diffusion |
| 12. | Glucose | Yellow | Blue-Green |
| 13. | Mannitol | Yellow | Blue-Green |
| 14. | Inositol | Yellow | Blue-Green |
| 15. | Sorbitol | Yellow | Blue-Green |
| 16. | Rhamnose | Yellow | Blue-Green |
| 17. | Saccharose | Yellow | Blue-Green |
| 18. | Melibiose | Yellow | Blue-Green |
| 19. | Amygdaline | Yellow | Blue-Green |
| 20. | Arabinose | Yellow | Blue-Green |

It is also possible to perform an oxidase (OXI) test as an additional test. This test can be performed in either chamber No. 1 (ONPG) or No. 6 ($H_2S$) whenever either is negative. As used herein, this test will be referred to as test No. 21.

Referring to FIG. 7, which is an outline of the method of this invention, the test results are arranged into a plurality of groups. It has been found to be preferable to arrange the tests into groups of three. Thus the above twenty-one tests would produce seven groups of three tests each.

While the arranging by groups of three tests each is not essential, the number within a group should maximize both simplicity and efficiency. For example, should the tests be segrated into groups of four tests each, the resulting numerical profile will either be in hexadecimal notation, which could be more difficult to the untrained or will entail more than a single digit. Larger groupings could become absurd. Should smaller groupings be selected, then more digits will be required than by the grouping by threes. The grouping by three tests each of the method of this invention enables the transforming of the test results of the group into a single score such as a single digit. Each test within a group can be assigned a weighted score. The selection should be made so that the sum of any combination of scores is unique and preferably of a single digit. For example, assigning a score of zero to all negative results and score of 1, 3 and 5 to positive results of each of the three tests, respectively, will produce a unique set of such sums.

While any such set of scores will suffice, it is preferred to assign the following scores. These twenty-one tests of the API Enteric System plus the oxidase test are divided into seven groups of three:

| ONPG | ODC | URE | VP | MAN | RHA | AMY |
| --- | --- | --- | --- | --- | --- | --- |
| ADH | CIT | TDA | GEL | INO | SAC | ARA |
| LDC | H₂S | IND | GLU | SOR | MEL | OXI |

After the results have been reported, a score is given to each positive result:

A score of ONE for the first biochemical of any group of three (i.e., ONPG, ODC, URE ... )

A score of TWO for the second biochemical of any group of three (i.e., ADH, CIT, TDA ... )

A score of FOUR for the third biochemical of any group of three (i.e., LDC, H₂S, IND ... )

All negative tests score zero, producing the following for each combination of results:

| Test Results | Sum |
| --- | --- |
| All negative | 0 |
| No. 1 positive, No. 2, 3 negative | 1 |
| No. 2 positive, No. 1, 3 negative | 2 |
| No. 1, 2 positive, No. 3 negative | 3 |
| No. 3 positive, No. 1, 2 negative | 4 |
| No. 1, 3 positive, No. 2 negative | 5 |
| No. 2, 3 positive, No. 1 negative | 6 |
| All positive | 7 |

Each digit of the seven-digit number is obtained by totaling the score of the positive reaction of each group of three. Example: 5 044 552 = E. coli

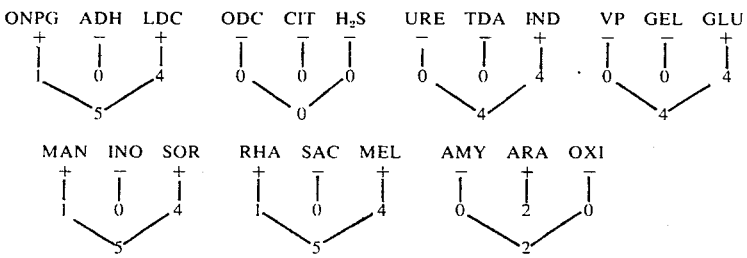

It should be noted that each number corresponds to only one combination and, therefore, for each seven-digit number there will be only one corresponding profile.

In effect, this selection of scores results in the conversion of the binary results (positive or negative) of each test into a single octal digit. Thus, the grouping of these twenty-one tests in the API Enteric System into groups of three will produce seven individual octal digits which will characterize all twenty-one tests. Thus the user characterizes each test as positive or negative and assigns the score for each test in the group. Then the scores for each in the group are added together, thereby producing a one-digit number. For example, if in group 4, test 10 is positive, 11 is negative and 12 is positive, then test 10 has a score value of one, test 11 scores zero, and test 12 scores four. Adding the scores together, the score of five is obtained for test grouping number 4.

The digits representing the sum of the scored for each test group are combined to form a seven-digit octal number. The seven digits are written down sequentially. Thus, the digit from test group 1 becomes the high order digit, the digit from test group 2 is next, etc., and the digit from test group 7 becomes the lowest order digit. Naturally any similar predetermined method of combining these digits will suffice. The seven-digit number thus produced is the Profile Recognition Number.

A Profile Register 18 (FIG. 7) of sequentially listed Profile Recognition Numbers is then consulted and the bacterium identified. As an example, if tests 1, 9, 12, 13, 18 and 20 are positive and the remainder of tests negatives, the identification proceeds as follows:

Group No. 1 has its first test positive and second and third negative and gets a score of 1.

Group No. 2 is all negative and receives a score of 0.

Group 3 has its third test positive and others negative and receives a score of 4.

Group No. 4 also has its third test positive and others negative and receives a score of 4.

Group No. 5 has its first test positive only and receives a score of 1.

Group No. 6 has its third test positive only and receives a score of 4.

Group No. 7 has its second test positive, others negative and receives a score of 2.

Combining all digits produces the Profile Recognition Number 1044142. The Profile Register identifies this number as being associated with the bacterium E. coli.

A profile Register of pre-identified profiles has been established. The establishment of these pre-identified profiles has first been performed on a theoretical basis and then matched with more than 25,000 results obtained using the API 20 Enteric device.

Initially a theoretical register has been established based on percentage data which has been previously reported in technical publications. Reactions have been considered as variable whenever a percentage of positive reactions was 95% or less. Profile numbers have been established considering all possible combinations obtained by permutation of the variable reactions. If, for example, three reactions were variable, eight profile numbers have been established. For eight variable reactions, 256 profile numbers have been established. The purpose of this theoretical register was to determine the possibility for one profile number to correspond to more than one organism. Because twenty biochemicals are considered simultaneously, we encountered very few such occurrences.

Results obtained on this system, mainly from clinical laboratories, have been gathered. These results came mainly from the following countries: the United States, Canada, France, England and Germany. Inasmuch as possible, results have been gathered from several geographical areas. For example, results from the U.S. were obtained from the following states: California, Georgia, Louisiana, Maine, Michigan, Minnesota, Nebraska, New Jersey, Texas and Washington, D.C.

Whenever more than one organism name has been reported for the same profile number, consideration of theoretical results and probability have been considered and whenever necessary and possible, the organism has been run through the API 50 Research system which provides for a profile based on fifty biochemicals.

Whenever organisms could not be separated on the basis of the 20 biochemicals, reference is being made to a note which suggests complementary tests required to separate such organisms.

The Profile Register is used as follows:

After a profile number has been recorded, either using the mathematical conversion method or the Coder device 22 (FIG. 4), discussed below, the number is then searched in the Profile Register.

1. Whenever a number of an unknown is matched with a number of the Profile Register, there is an extremely high probability that the designation of this organism is the one indicated by the Profile Register. The three last digits of the profile number may appear in either small or larger typeface, or in large typeface underlined. The underlined large typeface indicates a very common biotype. The large type (without underlining) indicates a common biotype and the small typeface indicates a rare biotype.

Example: 5144552- E. coli -very common biotype
5144550 - E. coli -common biotype 5 004 552 - E. coli -rare biotype (IND -)

2. Whenever a number refers to another number, it is implied that a biochemical test has been misinterpreted. The user should refer to the correct number for proper identification and go back to the misinterpreted results for further improvement of color interpretation.
Example: 7 304 733 - See 5 304 733
The difference is only the first digit

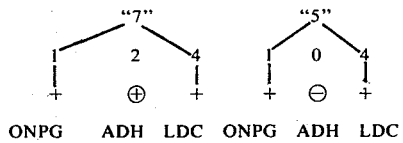

This indicates that the arginine of orange color should have been interpreted as negative for S. liquefaciens.

3. If the number obtained is not in the Register, the number should first be rechecked using both the mathematical and Coder approaches. If the number is still not in the Register, it will mean that the strain is a very rare biotype which has not yet been listed in the Register or that there is an error in the laboratory procedure. In this case, the approach of a diagnosis by elimination should be considered and, if not conclusive, a new test strip should be rerun after a new isolation has been made and the results compared. If the number then obtained is the same as initially which does not fit any preset pattern, this organism should be sent to competent authorities for further identification. At this time, the use of the API 50 Research system can prove to be very useful.

When an organism does not fit the profile expected, diagnosis by elimination can be considered. This approach is to try to match the unknown profile with each of the species of the familty Enterobacteriaceae and see the reason why this unknown profile cannot be successively each of them.

The selection system, as discussed below, has been based on the experience gathered in studying more than 25,000 organisms for the establishment of the Profile Register. The numbers indicated in black for each organism are numbers which correspond to very common biotypes. The black numbers in any column represent about 90% of the organisms encountered for this specie. The numbers indicated in blue are numbers representing very seldom encountered biotypes. These blue numbers represent percentages of occurrence generally between 1 and 5%.

EXAMPLE:

0 054 210 — This profile is not found in the Profile Register. The use of the Selector will permit the following deduction and elimination:

a. because of its two first digits, "0 0", this unknown should not be S. sonnei, Salmonella, P. mirabilis, P. morganii, KES group, Citrobacter species. Actually, what we are saying is that the above-mentioned organisms must have at least one positive reaction within the first six biochemical tests on the API 20 Enteric system. By elimination, it can only be: E. coli, Shigella, P. vulgaris, P. rettgeri, Providencia, Pectobacterium, Y. enterocolitica.

b. because of its third digit, "5", this unknown should not be E. coli, Shigella, Providencia. By elimination, it can only be: P. vulgaris, P. rettgeri, Pectobacterium or Y. enterocolitica.

c. the fourth digit, "4", is of no assistance to eliminate any of these four organisms.

d. the last three digits, "210", eliminates Pectobacterium and Y. enterocolitica. This unknown can therefore theoretically be either a P. vulgaris or a P. rettgeri. We can now consider what the highest probability for each of these organisms is by counting the black and blue figures.

| | | |
|---|---|---|
| P. vulgaris | 3 black | 4 blue |
| P. rettgeri | 5 black | 2 blue |

The highest probability is that this organism is a P. rettgeri which can be verified by checking the result with the API Per Cent Chart.

Referring now to FIG. 4, the apparatus represented therein is the preferred form of a coder 22 to partially automate the above method. The coder allows the conversion of positive and negative results into the Profile Recognition Number.

Preferred embodiments of the Coder as shown in FIGS. 4, 5 and 8 comprise a base member 22a fixedly attached on three sides to a cover member 22b, in such manner as to form a support frame and to leave a thin flat elongated chamber 22c defined by these members. The material may be any convenient one such as acrylic (Plexiglass) material, but should be fairly rigid and is preferably opaque. A plurality of rib members 22d are fixedly attached within the defined chamber to provide for a plurality of equal sized chambers. It is most convenient for carrying out the above method if the rib, base and cover members define seven individual chambers as shown in FIG. 4. The embodiment shown in FIG. 8 where five individual chambers are used is the preferred embodiment of the Coder when using the fifty test method, described below.

A slidably mounted flat member 23 or slide is fitted into each of the chambers 22c. Thus if seven chambers are provided, seven slide members 23 are provided. The slide members can be of such size as to fit closely to the dimensions of the chambers as to be held therein by friction, for example, should the entire apparatus be disposed with the open slide downward. Conversely each slide member can be easily moveable by means of a pencil, probe, stylus or the like 24, inserted in indentations 23a in each slide member (FIG. 6). The number of chambers and number of slide members may differ from seven when using other than the API Enteric System. The seven slide members of the apparatus of this invention correspond to the seven test groups described in the above method. Thus, while each slide member is structurally identical to each other slide member, each may differ in marking in accordance with the specific biochemical test represented thereon.

FIG. 6 is a representation of the seven slide members corresponding to the 21 tests of the API Enteric System described above. Each slide member 23 is generally of elongated rectangular top surface with a thickness adopted to fit its related chambers.

The slides 23 are fitted with a plurality of indentations 23a in order that the slide may be moved by inserting the tip of the stylus and pushing the slide. These are disposed into three columns of equally spaced indentations. The three columns represent the three tests of the group. Should some other grouping be used, suitable modification must be made in the slide member. Each slide member is also imprinted thereon with the possible digits 23b representing the sum of the scores for each test. When used with the illustrative tests described herein, the digits will be 0 through 7. The digits are placed on the slide member in such order that the correct digit will be generated whenever the slide member is moved in accordance with the instructions below. For the API Enteric System, they are placed sequentially, reading from the bottom of the member as shown in FIG. 6.

The cover member 22b shown in FIG. 4 contains a series of three slots 25, 26, 27 corresponding to each slide 23. There is also a window 28 overlying each slide member. The slots are in appropriate lengths or increments to linearly represent the scores designated for each of the three tests of the group. With the system herein described, the slots 25, 26, 27 generally have lengths or increments in the ratio of 1:2:4 respectively. The slots 25, 26, 27 and the window 28 are disposed in such manner that when the slide member is mounted in the Code 22, apparatus the indentations in the slide member are accessible through the slots and one digit imprinted on the slide member is visible through the window.

The cover member 22b may also contain 21 additional windows 29 disposed in such manner that three correspond to each slide member. The number of such windows will be the same as the number of tests being performed. Each slide member is provided with three columns 30, 31 and 32 of eight areas 30a–h, 31a–h and 32a–h, respectively, each for color coding. When the slide member is inserted into the apparatus, one color area of each column on the slide member will be visible through the corresponding window 29 in the cover member.

The colored areas can be determined as follows:

Color column 30 relates to the first test of the test group and color areas 30a, 30c, 30e and 30g (from bottom) of the column are colored the negative color of this test, while areas 30b, 30a, 30f and 30h receive the positive reaction color.

Column 31 relates to the second test of the group. Areas 31a, 31b, 31e and 31f are imprinted with the negative color and areas 31c, 31d, and 31g and 31h with the positive.

Column 32 relates to the third test of the group. Areas 32a, 32b, 32c and 32d are in the negative color and areas 32e, 32f, 32g and 32h are in the positive one.

Each biochemical reaction corresponds to a slot (25, 26, or 27) and window 29 on the cover 22b (FIG. 4). Each group of three reactions corresponds a slide 23 and a window 28. The operating principle of the coder 22 is to move the slide parts only when the reactions are positive. The apparatus is made ready for use by having all slide members fully inserted into the base-cover combination. At this time, the digits 23b (FIG. 6) visible in each of the windows 28 (FIG. 4) must be zero. Likewise, the colors visible in windows 29 must all be the colors indicating the negative for each reaction. The cover member 22b identifies each elongated hole 25, 26 and 27 and each window 29 with the test to which it corresponds. These are arranged in numerical order from left to right or viewed in FIG. 4.

The reactions are reported from the left to the right. When a reaction is positive, the pen is inserted in the upper part of the slot and lowered to the extremity of the slot, moving the slide therewith. If a reaction is negative, the sliding part remains unmoved. After each reaction has been reported, a color matching the positive reaction obtained on the API strip should appear in the corresponding opening.

After each group of three biochemicals have been reported, the opening on the lower part corresponding to the three biochemicals will show the proper number which will be one of the seven digits number. Upon completion of recording of the 21 biochemical reactions, the Coder 22 will provide the user with a seven digit number visible in the seven windows 18.

The Coder has a built-in verification system which allows the matching of color patterns obtained on the test strip 11 with the color pattern obtained on the Coder 22 after the slide members have been moved in accordance with instruction. The colors are visible in windows 29.

In case a reaction has been mis-recorded, it is suggested that the three reactions corresponding to the sliding part where the mistake occured be placed back into original position and the three reactions recorded properly. For example: If the reaction ADH is mis-reported, it is recommended that the first slide member corresponding to the reaction ONPG, ADH, LDC be placed in its original position.

After completion of the reporting, the API Coder should be returned to its initial position by placing the Coder vertically and pushing it down in order to reinsert the sliding members.

FIFTY TEST METHOD

As hereinbefore stated, the method of this invention may be used to interpret the results from any number of tests. It has been found that a particularly sensitive test result may be obtained when using a series of fifty tests.

The following purely illustrative description will illustrate the use of one fifty-test method for the identification of Enterobacteriaceae.

Test strips, essentially similar to that illustrated in FIG. 8, are available commercially from Analytab Products, Inc., Carle Place, New York 11514 and sold under the name API 50 Research System.

The following description will illustrate the method of the invention using the API 50 Research System. It is understood, however, that any similar set of tests may be utilized.

It is not necessary that the user utilize a commercially available test strip. It is within the intent and scope of this invention to describe a method of conversion of test results into a numerical profile. It is entirely possible to utilize no prepared test strip, but to perform the individual tests separately in culture tubes or the like. This latter procedure will however, reduce the speed and convenience of the overall method.

The ordering of the tests on the test strip is of no consequence as all tests are performed simultaneously and are given equal weight in evaluating the results. However, it is necessary to arbitrarily preselect a given sequence and to adhere to that sequence. The Profile Register tabulations will depend on the order selected.

The API 50 Research System utilizes the following fifty tests in the order listed.

1. phenol red-control tube
2. glycerol
3. erythoritol
4. d(−) arabinose
5. L (+) arabinose
6. ribose
7. d (+) xylose
8. L (−) xylose
9. adonitol
10. methyl-xyloside
11. galactose
12. d (+) glucose
13. d (+) levulose (fructose)
14. d (+) mannose
15. L (−) sorbose
16. rhamnose
17. dulcitol
18. meso-inositol
19. mannitol
20. sorbitol
21. methyl-d-mannoside
22. methyl-d-glucoside
23. N acetyl-glucosamide
24. amygdalin
25. arbutine
26. esculine
27. salicin
28. d (+) cellobiose
29. maltose
30. lactose
31. d (+) melibiose
32. saccharose (sucrose)
33. d (−) trehalose
34. inuline
35. d (+) melizitose
36. d (+) raffinose
37. dextrine
38. amylose
39. starch
40. glycogen
41. ONPG
42. arginine
43. lysine
44. ornithine
45. citrate
46. thiosulfate
47. urea
48. tryptophane
49. tryptophane-peptone
50. pyruvic acid Reaction chambers Nos. 1–25, 25–40, 42–44 and 47 also contain phenol red as an indicator. The material in reaction chamber No. 25 includes a mixture of phenol red and ferric chloride and chamber No. 26 contains ferric chloride as indicators. Reaction chambers Nos. 41, 45–46 and 48–50 do not contain an indicator.

The above-described test strips are particularly designed for the determination of enterobacteriaceae. The first forty tests are carbohydrate fermentations. The same test strips may also be used for the identification of bacterial families for which carbohydrate metabolism is important, such as streptococcus, staphylococcus, pasteurelleae, vibrionaceae and some pseudomanadaceae.

Tests 41 through 50 are identical to tests 1–10 of the previously described API Enteric System.

The test strips for the API Research System include nutrients in reaction chambers Nos. 41–50. No nutrient is included in reaction chambers Nos. 1–40, thereby providing a greater versatility to the test strips. The user can then utilize differing nutrient media depending on the particular bacterium being tested.

The bacterium may be cultured by any convenient method. If it is cultured on an agar plate, small sections may be selected with a wire loop for suspension. If cultured in a liquid medium, then it is preferable to centrifuge the liquid to obtain a more concentrated culture. In any event, it is necessary to use proliferant bacteria in an exponential phase growths.

The sample of culture bacteria is then suspended into a suitable medium. It is necessary to prepare two different suspension media for use with this test strip.

The first suspension is prepared for use in research chambers Nos. 1-40. These chambers do not contain any culture medium. Hence the bacterial suspension for use with these chambers must include the culture medium. In this manner, the system has a greater flexibility of use with different types of bacteria, by allowing the use of differing culture media depending on the suspected identity of the unknown bacterium.

The culturing medium selected must be rich enough to promote the rapid growth of the bacteria. It should not contain any fermentative substances and preferably has a pH of about 7.4. Classical culturing media may be used. For example, when the bacterium is a suspected enterobacteriaceae a standard peptane broth may be used. It is preferable to use a peptane broth enriched with yeast extract when the unknown bacterium is suspected to be one which is more difficult to grow, such as a streptococcus.

The bacterial culture suspension should be sufficiently dense to permit multiplication, but not excessively dense. Generally, its optical density should be about the same as tube 1 of the standard McFarland optical density scale.

The McFarland scale is prepared by introducing different quantities of 1% barium chloride and 1% sulfuric acid into ten identical tubes. For example, ten 16mm test tubes are used. It is convenient if they are graduated to contain 10ml. 0.1 ml. of the barium chloride solution is introduced into the first tube, 0.2ml. into the second and so on up to 1.0ml. added to the tenth tube. Each tube is then filled to the 10ml graduation with the sulfuric acid solution, the tube stoppered and the contents thoroughly mixed. It will be necessary to shake the tubes prior to each use to distribute the sediment throughout the liquid. The bacterial suspension and the McFarland standard tubes are then visually compared.

If both oxidation and fermentation of the bacterium in the presence of the various carbohydrates is studied, then the suspension medium is preferably 0.7% agar. The suspension is prepared by warming the medium to about 40°C and the bacterial culture introduced. The suspension must then be inoculated into the reaction chambers while still likewarm, before gelification.

Reaction chambers Nos. 41–50 contain, in addition to the aforementioned materials, the culture medium. Hence none is to be added to the bacterial suspension designed for use in these chambers. It is preferable that the bacteria be suspended in either distilled water or normal saline solution. A suspension having an optical density of tube 1 on the McFarland scale is preferable.

The reaction chambers are inoculated by introducing the appropriate bacterial suspension into the interior of each reaction chamber, such as by use of a Pasteur pipette. Care should be taken to avoid the introduction of air bubbles into the suspension.

It is preferable that each reaction chamber be filled properly. The quantity of suspension to be introduced will vary with the suspected identity of the unknown bacterium.

Referring again to FIG. 3, each reaction chamber 15 can be visualized as being divided into regions: the tube section 15a, and the cupule 15b, which is that region encircled by flange 17.

Reaction chambers Nos. 1–40 are preferably filled with the bacterial suspension in the following manner. It is generally only necessary to fill the tube region with the suspension. However, if the suspected identity of the bacterial family is one which is known to produce either volatile acids or relatively small quantities of acids, such as Streptococcus and Pasturella, the chamber should be sealed by filling the cupule with sterile paraffin oil. When the unknown bacterium is suspected to be one which both grows and produced acid, then both the tube region and the cupule are filled with the suspension. It is with such bacteria that the preferred culture medium is the ag 2.

Reaction chambers Nos. 41–50 are filled as follows regardless of the suspected identity of the bacterium.

In reaction chambers Nos. 41–44 and 46–49, only the tube region is filled. Both the tube region and the cupule are filled in chambers Nos. 45 and 50. Reaction chambers Nos. 42–44 and 47 should be sealed by filling the cupule with sterile paraffin oil.

The inoculated test plate is then incubated in the same manner as described for the API Enteric System. It is preferable to incubate the test plate for at least 18 hours before making a determination of the results.

After the proper incubation period a determination is made of whether the bacterium has or has not reacted with each test reagent.

Prior to making this determination, several drops of Ferric chloride are added to chamber No. 48; several drops of Kovaks reagent to chamber No. 49 and several drops of a potassium hydroxide- and α-napthol solution to chamber No. 50.

The determinations of evidence of reaction are made by visually observing the color of the material in a manner similar to that described for the API Enteric System.

| Test | | Positive | Negative |
|---|---|---|---|
| 1. | Phenol red | remains red | |
| 2. | Glycerol | yellow | red |
| 3. | Erythoritol | yellow | red |
| 4. | d(−) Arabinose | yellow | red |
| 5. | L(+) Arabinose | yellow | red |

-continued

| Test | | Positive | Negative |
|---|---|---|---|
| 6. | Ribose | yellow | red |
| 7. | d(+) Xylose | yellow | red |
| 8. | L(−) Xylose | yellow | red |
| 9. | Adonitol | yellow | red |
| 10. | Methyl-xyloside | yellow | red |
| 11. | Galactose | yellow | red |
| 12. | d(+) Glucose | yellow | red |
| 13. | d(+) Levulose (Fructose) | yellow | red |
| 14. | d(+) Mannose | yellow | red |
| 15. | L(−) Sorbose | yellow | red |
| 16. | Rhamnose | yellow | red |
| 17. | Dulcitol | yellow | red |
| 18. | Meso-inositol | yellow | red |
| 19. | Mannitol | yellow | red |
| 20. | Sorbitol | yellow | red |
| 21. | Methyl-d-mannoside | yellow | red |
| 22. | Methyl-d-glucoside | yellow | red |
| 23. | N-acetyl-glucosamide | yellow | red |
| 24. | Amygdalin | yellow | red |
| 25. | Arbutine | yellow-black | red |
| 26. | Esculin | black | colorless |
| 27. | Salicin | yellow | red |
| 28. | d(+) cellobiose | yellow | red |
| 29. | Maltose | yellow | red |
| 30. | Lactose | yellow | red |
| 31. | d(+) Melibiose | yellow | red |
| 32. | Saccharose (sucrose) | yellow | red |
| 33. | d(−) Trehalose | yellow | red |
| 34. | Inuline | yellow | red |
| 35. | d(+) Melizitose | yellow | red |
| 36. | d(+) Raffinose | yellow | red |
| 37. | Dextrine | yellow | red |
| 38. | Amylose | yellow | red |
| 39. | Starch | yellow | red |
| 40. | Glycogen | yellow | red |
| 41. | ONPG | yellow | colorless |
| 42. | Arginine | red | red |
| 43. | Lysine | red | yellow |
| 44. | Ornithine | red | yellow |
| 45. | Citrate | blue | green |
| 46. | Thiosulfate | black | colorless |
| 47. | Urea | red | yellow |
| 48. | Tryptophane | brown | yellow |
| 49. | Tryptophane-peptane | red rind | yellow red |
| 50. | Pyruvic acid | bright red | colorless |

Each determination that a reaction has assigned is assigned a value of + and each determination is assigned a value of −.

It is most convenient to group the fifty tests in groups of five. Thus, ten such groups are assigned. For example, the first group would include the following five determinations.

1. Phenol red
2. Glycerol
3. Erythritol
4. d(−) Arabinose
5. L(+) Arabinose

For each group, there are 32 possible combinations of determinations of whether the specimen has or has not reacted. A set of 32 digits or intermediate values has been selected to represent each of the 32 conditions within each group. Each digit thus represents the results of one group of five tests.

The following list of digits has been selected. To avoid confusion, the letters i and o, and the numbers 1 and 0 have not been used. Of course, any list of representations may be used, but once selected, the same list must always be used.

LISTING OF 32 SYMBOLS

| | | | | | |
|---|---|---|---|---|---|
| A | − | − | − | − | − |
| B | + | − | − | − | − |
| C | − | + | − | − | − |
| D | − | − | + | − | − |
| E | − | − | − | + | − |
| F | − | − | − | − | + |
| G | + | + | − | − | − |
| H | − | + | + | − | − |

LISTING OF 32 SYMBOLS-continued

| | | | | | |
|---|---|---|---|---|---|
| J | − | − | + | + | − |
| K | − | − | − | + | + |
| L | + | − | + | − | − |
| M | − | + | − | + | − |
| N | − | − | + | − | + |
| P | + | − | − | + | − |
| Q | − | + | − | − | + |
| R | + | − | − | − | + |
| S | − | + | + | + | − |
| T | + | − | + | + | − |
| U | − | + | + | − | + |
| V | + | + | − | + | − |
| W | + | − | + | − | + |
| X | − | + | − | + | + |
| Y | + | + | + | − | − |
| Z | + | + | − | − | + |
| 2 | + | − | − | + | + |
| 3 | − | − | + | + | + |
| 4 | + | + | + | + | − |
| 5 | + | + | + | − | + |
| 6 | + | + | − | + | + |
| 7 | + | − | + | + | + |
| 8 | − | + | + | + | + |
| 9 | + | + | + | + | + |

Thus, for example, if in the first group there is a positive reaction with Erythritol and none with the other reagents, the representation for the group would be:

− − + − − which yields the value of "D" from the listing.

A similar determination is then made for each of the ten groups of determinations. The ten digits thus selected are combined to form a ten digit numerical representation which is indicative of the identity of the unknown bacterium. A preferred method of generating this numerical representation or final value is to list the intermediate values in identical order to that in which they are generated, starting with the lowest order test numbers.

For example, if after incubation, the following tests yield a positive result:
  2. Glycerol
  6. Ribose
  11. Galactose
  12. d(+) Glucose
  13. d(+) Levulose
  14. d(+) Mannose
  16. Rahmnose
  18. Meso-inositol
  19. Mannitol
  20. Sorbitol
  23. N acetyl-glucosamide
  24. Amygdalin
  25. Arbutine
  26. Esculin
  27. Salicin
  28. d(+) Cellobiose
  29. Maltose
  30. Lactose
  32. Saccharose
  33. d(−) Trehalose
  35. d(+) Melizitose
  41. ONPG
  42. Arginine and the remainder negative, the result would be:

| Group | Results | | | | | Value |
|---|---|---|---|---|---|---|
| 1 | − | + | − | − | − | C |
| 2 | + | − | − | − | − | B |
| 3 | + | + | + | + | − | 4 |
| 4 | + | − | + | + | + | 7 |
| 5 | − | − | + | + | + | 3 |
| 6 | + | + | + | + | + | 9 |
| 7 | − | + | + | − | + | U |
| 8 | − | − | − | − | − | A |
| 9 | + | + | − | − | − | G |
| 10 | − | − | − | − | − | A | and the final value would be:

CB473 9UAGA

A Profile Register has been established for the API 50 Research System in similar manner to that established for the API Enteric System. Consulting the Profile Register for this system, CB473 9UAGA = Streptococcus It is important to realize that the results of the determination may depend upon the nature of the culture medium in which the bacterium is suspended. It is thus a further feature of the Profile Register to enable the user to obtain the correct identification of regardless of the culture medium used.

It has been found convenient to identify the correct tabular listing by means of color coding the printing in the Profile Register. For example, the following printing colors can be utilized:

| Suspension Medium | Print Color |
|---|---|
| tryptocose broth | Black |
| yeast extract broth | Blue |
| nitrated broth | Green |

While the above color-coding method has proven convenient, the same result can be obtained by other means, such as by using standard type, italics, bold face, etc.

The step of converting the score values for each group of determinations into the intermediate value can also be performed in a manner similar to the mathematical method described for the example of the API Enteric System.

When using such method with the API 50 Research System, the determinations are grouped in groups of five test each. Each of the five tests within the group is then assigned a weighted score value.

It is convenient to assign score values to each determination where the first determination within a group receives a score value of 1, the second a score value of 2, the third 31 4, the fourth −8 and the fifth −16. The intermediate value can then be the sum of the score values within the group. This method is inconvenient as the intermediate value for each group may not be a single digit.

However, this method of forming the intermediate value is utilized when using a mechanical coder device similar to that used for the API Enteric System.

A coder device useful with the 50 test system could be constructed utilizing ten chambers and slide members, each corresponding to a single test group. However, such coder would be cumbersome and unwiedly. It is thus preferable to utilize a coder having only five slide members, wherein score values of the first five groups of determinations are converted to the five intermediate values, the slide members replaced and the process repeated for the second set of five groups.

Referring to FIG. 8, the preferred form of the coder used with the 50 test system is generally constructed similarly to the coder (FIG. 4) used with the 21 test system.

Five chambers 22c are provided into each of which a single slidably mounted flat member 23 is fitted.

FIG. 9 is a representation of a single slide member 23 adapted for use with the coder of FIG. 8. Each slide member is designed to fit snugly into its respective chamber in the coder.

Each slide member is fitted with a plurality of indentations (not shown) in order that the slide may be moved by inserting the top of a stylus and moving the slide. These are disposed in five columns of equally spaced indentations. The five columns represent the five tests of the group.

Each slide member is also imprinted with a set of indicia 41, representing the 32 possible combinations of test results within the group. The indicia are ordered as shown to be consistent with the method previously described for converting the score value to the intermediate value and to allow the use of the same Profile Register.

The cover member 22b (FIG. 8) contains a series of five slots 42, 43, 44, 45, 46 corresponding to each slide. There is also a window 47 overlying each slide member. The slots are of such lengths as to linearly represent the weighted score value for each test within the group. Generally, for the described system, they will be in the ratio of 1:2:4:8:16. The slots are disposed in such manner as to allow the tip of a stylus to be inserted through the slot into the indentations in the slide member. The window 47 is disposed in such position so that one of the indicia 41 is visible through the windows.

The cover member 22b may also contain five additional windows 48 for each chamber 22c. Each slide member has imprinted thereon five columns 49 of 32 characters each. When the slide member is inserted into each chamber, one character from each column is visible through each window 48.

The coder device of the 50 test system is operated in a manner similar to that described for the 20 test system. The intermediate value for each group of tests is read through windows 47.

The characters 49 visible through windows 48 provide a check for the operator. The characters visible through these window will correspond to whether the unknown bacterium has or has not reached. A − visible through the window can indicate an absence of reaction and a + the presence of reaction.

These areas on the slide can of course be color coded with the colors indicating whether the bacterium has or has not reacted, as described previously.

A generally similar test plate is also commercially available from Analytab Products, Inc., Carle Place, New York, which is adopted for use with Lactobacillus. In this system, the following tests are utilized, and the corresponding colors.

| Test | Positive | Negative |
| --- | --- | --- |
| 1. Bromcresol purple | remains purple | |
| 2. Glycerol | yellow | purple |
| 3. Erythoritol | yellow | purple |
| 4. d(−) Arabinose | yellow | purple |
| 5. L(+) Arabinose | yellow | purple |
| 6. Ribose | yellow | purple |
| 7. d(+) Xylose | yellow | purple |
| 8. L(−) Xylose | yellow | purple |
| 9. Adonitol | yellow | purple |
| 10. Methyl-xyloside | yellow | purple |
| 11. Galactose | yellow | purple |
| 12. d(+) Glucose | yellow | purple |
| 13. d(+) Levulose (Fructose) | yellow | purple |
| 14. d(+) Mannose | yellow | purple |
| 15. L(−) Sorbose | yellow | purple |
| 16. Rhamnose | yellow | purple |
| 17. Dulcitol | yellow | purple |
| 18. Meso-inositol | yellow | purple |
| 19. Mannitol | yellow | purple |
| 20. Sorbitol | yellow | purple |
| 21. Methyl-d-mannoside | yellow | purple |
| 22. Methyl-d-glucoside | yellow | purple |
| 23. N-acetyl-glucosamide | yellow | purple |
| 24. Amygdalin | yellow | purple |
| 25. Arbutine | yellow black | purple |
| 26. Esculin | black | colorless |
| 27. Salicin | yellow | purple |
| 28. d(+) cellobiose | yellow | purple |
| 29. Maltose | yellow | purple |
| 30. Lactose | yellow | purple |
| 31. d(+) Mellibiose | yellow | purple |
| 32. Saccharose (sucrose) | yellow | purple |
| 33. d(−) Trehalose | yellow | purple |
| 34. Inuline | yellow | purple |
| 35. d(+) Melizitose | yellow | purple |
| 36. d(+) Raffinose | yellow | purple |
| 37. Dextrine | yellow | purple |
| 38. Amylose | yellow | purple |
| 39. Starch | yellow | purple |
| 40. Glycogen | yellow | purple |
| 41. Arginine | red | yellow |
| 42. Glucose | bubbles | no bubbles |
| 43. Teepol 0.4% | growth-yellow | inhibition-purple |
| 44. Teepol 0.6% | growth-yellow | inhibition-purple |
| 45. Na Cl 4% | growth-yellow | inhibition-purple |
| 46. Na Cl 6% | growth-yellow | inhibition-purple |
| 47. Na Cl 10% | growth-yellow | inhibition-purple |
| 48. ONPG | yellow | purple |
| 49. $KNO_3$ + glucose | red | colorless |
| 50. Pyruvic Acid | red | colorless |

The color indicator for audification used in this system is bromcresol purple, which is included in reaction chambers Nos. 1–25, 27–40 and 42–47. Phenol red is used in chamber No. 41 and iron citrate is present in chambers Nos. 25 and 26.

This system is particularly designated to enable the user to determine the particular strain of the lactobacillus.

The invention includes a method for the identification of lactobacilli by cultural and biochemical characteristics. It can also be used for the identification of lactic streptococci and leuconostoc (betacocci).

To obtain reproduceable results, the experimental conditions must remain identical. These are generally easy to obtain. All the strains are grown on the same medium, during the same time and at the same temperatures. The in-growth culture is washed by centrifugation. With the sediment, a bacterial suspension is prepared in the "identification" medium defined by its optical density or numeration. The suspension is inoculated in each of the microtubes of identical capacity. During incubation, the speed of the appearances of the biochemcial reactions is reported on a result sheet forming a profile (FIG. 10). A comparison of the obtained profile with the reference profile enables control of the production.

It is necessary to employ a satisfactory nutritional medium. The identification can only be performed on strains which are in continuous growth for several days and in the phase of exponential growth.

The suspensions prepared should contain an identical number of bacteria. The optic density can be measured with a photometer (at 525 nm the appropriate density is about 0.200 in a 1.0 cm cell). For greater precision, particularly in the suspension of the industrial production of the same strain, the bacteria are counted by using a Coulter counter. For practical usage, the density can be compared to the McFarland scale.

The plate 11 is sterile. Each plate contains 50 biochemical reactions. The plate is then placed into a plastic box provided with the plate and some water is poured into the bottom of the box to create a humid atmosphere.

Using a Pasteur pipette, all the tubes are filled avoiding the introduction of air bubbles. To do so, place the tip of the pipette on the side of the tube. The tube portion (0.12 ml) is filled on all the tubes except tube 50 where the tube and cup section are filled so that the reading can be performed in the cup (aerobic conditions). Two drops of sterile mineral oil are added to all the tubes underlined (0, 1, 2, etc.)

The plastic box containing the inoculated plate is closed and placed in the incubator. If the incubator does not circulate humid atmosphere, the box should be placed on one of the top shelves far from the heating units. The incubation is performed at 37°C except for the L. viridenscens when a temperature of 30°C is recommended.

In forming a profile, the results can be compiled on the result sheet 51. When the reaction is considered as positive, it is reported on the result sheet by blackening only the positive reactions corresponding to the time of appearance (See FIG. 10.).

TESTS 1 THROUGH 40 — FERMENTATION AND GROWTH

The acid production precedes the growth and is easier to read during the first 6 hour period. The changing from purple to yellow of the bromcresol purple is reported after 3 and 6 hours of incubation.

After 24 hours of incubation, the bacterial growth is also reported by observing an opaque deposit at the bottom of the tube when the plates are observed by transparence on a black background. This reaction appears in addition to the fermentation. With some species such as the THERMOBACTERIUM the bacterial growth is sometimes easier to read than the fermentation. Gas Production: The heterofermentative species are producing gas which forms small bubbles on the upper part of the tube from 6 to 24 hours of incubation. Some species produce more gas with the maltose than with the glucose and the gas production may be observed with other carbohydrates during fermentation.

The gas production will be read and reported in tube 42 (glucose) only.

The readings of the results after 3, 6 and 24 hours should be sufficient to enable the diagnosis. It is useless to report the results of the fermentation after 48 hours of incubation.

POSITIVE REACTION: YELLOW and GROWTH of the organism

NEGATIVE REACTION: PURPLE and NO GROWTH of the organism

The 50 biochemical reactions have been selected to enable the diagnosis of the group, the species and recognition of a strain from its profile.

DIAGNOSIS OF GROUPS

| TEST | THERMO-BACTERIUM | STREPTO-BACTERIUM | BETA-BACTERIUM |
|---|---|---|---|
| RIBOSE | − | + | + |
| ARGININ | − | − | + |
| GAS PRODUCTION IN GLUCOSE | − | − | + |

Under each profile the differentiating characteristics which enable one to diagnose the group are indicated by the following symbols:

● BLACK CIRCLES 52 for the tests which are positive.

○ WHITE CIRCLES 53 for the tests which are negative.

DIAGNOSIS OF THE SPECIES

Under each diagram the differentiating characteristics of the species are indicated by the following symbols:

▲ BLACK TRIANGLES 54 for positive reactions
△ WHITE TRIANGLES 55 for negative reactions
For example:

White circles under the ribose test arginin ADH and gas are a presumption of a THERMOBACTERIUM.

The black triangle under the maltose test on the L. helveticus profile differentiates this specie from the L. jugurti by the fermentation of this carbohydrate.

DIAGNOSIS OF A STRAIN

The profile of a strain must always remain identical to itself during the preparation, or at all times during the continuous culture. When the experimental conditions are carefully reproduced, it is possible to report a modification in the profile much faster than with conventional methods. The strain can be checked every hour or every two hours. As an example, the follow-up of a continuous culture of a L. helvecticus strain and its stopping because of a variation in the aspect of the profile.

What is claimed is:

1. In a method for the identification of an unknown substance, a specimen of the substance having been prepared to be analyzed, portions of the prepared specimen being caused to undergo a plurality of different tests, each test having a predetermined indicia when the specimen has not reacted and a different predetermined indicia when the specimen has reacted, the improvement which comprises:
   a. arranging the tests into at least one group which includes a plurality of individual test determinations, each test determination being assigned a score value, the score value for each determination being different depending upon whether the specimen has or has not reacted, the score value of each determination in a group being weighted differently for the condition when the specimen has reacted, and the sum of any combination of score values in a group being different from the sum of any other combination of score values within the group;
   b. comparing the predetermined indicia and the different predetermined indicia of each test to an apparatus having a supporting frame and at least one member corresponding to a group of determinations and containing a representation for the condition when the specimen has not reacted and a representation for the condition when the specimen has reacted, each member being divided into fixed increments, the magnitude of each increment being a function of the weighted score value for each determination in a group corresponding to the movable member, wherein sequential movements of the movable member provide a total movement representative of the combining of score values of the group and the correct indicia of reaction for each determination in a group;

c. in response to the step of comparing, moving each movable member through the increment for each determination in a group to which the movable member is related when the specimen has reacted, the moving of the movable member both exposing the representation for the condition when the specimen has reacted and forming a score value for each determination, the movable member being moved sequentially until a total group score value for each group is obtained, the representation of each movable member after moving enabling the representation to be checked against the predetermined indicia and different predetermined indicia of the test; and d. assembling the score values of all groups into a final value which is distinctive for each different combination of group score values, the final value being indicative of the identification of the unknown substance.

2. In a method in accordance with claim 1 in which the step of arranging the tests into at least one group comprises arranging the tests into groups containing equal numbers of determinations.

3. In a method in accordance with claim 1 in which each group includes three determinations.

4. In a method in accordance with claim 1 in which each group includes five determinations.

5. In a method in accordance with claim 1 in which the score value comprises a numerical score value.

6. In a method in accordance with claim 5 in which the numerical score value is zero for the condition in which the specimen has not reacted and a numerical score value different from zero for the condition in which the specimen has reacted.

7. In a method in accordance with claim 6 in which the numerical score value different from zero for each different determination in a group is weighted with an increasing numerical value in a predetermined manner.

8. In a method in accordance with claim 7 in which the numerical score value which is weighted with an increasing numerical value in a predetermined manner is weighted as a function of powers of a predetermined base.

9. In a method in accordance with claim 8 in which the predetermined base is two.

10. In a method in accordance with claim 5 in which each group includes three determinations and in which the numerical score value is zero for the condition in which the specimen has not reacted and a numerical score value of 1, 2, and 4 for the three determinations, respectively, for the condition in which the specimen has reacted.

11. In a method in accordance with claim 5 in which each group includes five determinations and in which the numerical score value is zero for the condition in which the specimen has not reacted and a numerical score value of 1, 2, 4, 8 and 16 for the five determinations, respectively, for the condition in which the specimen has reacted.

12. In a method in accordance with claim 5 in which each numerical score value of a group is mathematically combined with a preceding recorded score value.

13. In a method in accordance with claim 12 in which the numerical score values are mathematically combined by summation of the numerical score values, the resulting sum being the group score value.

14. In a method in accordance with claim 1 in which the step of assembling the score values of all groups into a final value comprises the step of placing the score value of all groups into different positions in accordance with a predetermined format, the format presenting the final value.

15. In a method in accordance with claim 14 in which the step of positioning the score values of all groups into a predetermined format comprises arranging the score values in a sequence in correspondence to the predetermined order of the groups.

16. In a method in accordance with claim 1 and further comprising the step of identifying the unknown substance by consulting a tabular register of possible final values.

17. In a method in accordance with claim 16, wherein the tabular register includes representations of the final values which are in at least one of a plurality of different predetermined forms, each different predetermined form corresponding to a different predetermined condition of the prepared specimen, and wherein the step of consulting the tabular register includes the step of consulting the predetermined form corresponding to the predetermined condition of the prepared specimen.

18. In a method for the identification of an unknown micro-organism, a specimen of the micro-organism having been prepared to be analyzed, portions of the prepared specimen being caused to undergo a plurality of different biochemical tests with different biochemical test reagents each test having a predetermined indicia when the specimen has not reacted and a different predetermined indicia when the specimen has reacted, at least certain of the reagents having a chemical reaction indicating substance, the improvement which comprises:

a. arranging the tests into at least one group which includes a plurality of individual test determinations, each test determination being assigned a score value, the score value for each determination being different depending upon whether the specimen has or has not been reacted, the score value of each determination in a group being weighted differently for the condition when the specimen has reacted, and the sum of any combination of score values in a group being different from the sum of any other combination of score values within the group;

b. comparing the predetermined indicia and the different predetermined indicia of each test to an apparatus having a supporting frame and at least one member corresponding to a group of determinations and containing a representation for the condition when the specimen has not reacted, and a representation for the condition when the specimen has reacted each member being divided into fixed increments, the magnitude of each increment being a function of the weighted score value for each determination in a group corresponding to the movable member, wherein sequential movements of the movable member provide a total movement representative of the combining of score values of the group and the correct indicia of reaction for each determination in a group;

c. in response to the step of comparing, moving each movable member through the increment for each determination in a group to which the movable member is related when the specimen has reacted, the moving of the movable member both exposing the representation for the condition when the specimen has reacted and forming a score value for each determination, the movable member being moved sequentially until a total group score value for each group is obtained, the representation of each movable member after moving enabling the representation to be checked against the predetermined indicia and different predetermined indicia of the test; and d. assembling the score values of all groups into a final value which is distinctive for each different combination of group score values, the final value being indicative of the indentification of the unknown substance.

19. In a method for the identification of an unknown bacterium, a specimen of the bacterium having been prepared to be analyzed, portions of the prepared specimen being caused to react with a plurality of tests with different biochemical test reagents each test having a predetermined indicia when the specimen has not reacted and a different predetermined indicia when the specimen has reacted, at least certain of the reagents having a chemical reaction indicating substance, the improvement which comprises:

a. arranging the tests into at least one group which includes a plurality of individual test determinations, each test determination being assigned a score value, the score value for each determination being different depending upon whether the specimen has or has not reacted, the score value of each determination in a group being weighted differently for the condition when the specimen has reacted, and the sum of any combination of score values in a group being different from the sum of any other combination of score values within the group;

b. comparing the predetermined indicia and the different predetermined indicia of each test to an apparatus having a supporting frame and at least one member corresponding to a group of determinations and containing a representation for the condition when the specimen has not reacted and a representation for the condition when the specimen has reacted, each member being divided into fixed increments, the magnitude of each increment being a function of the weighted score value for each determination in a group corresponding to the movable member, wherein sequential movements of the movable member provide a total movement representative of the combining of score values of the group and the correct indicia of reaction for each determination in a group;

c. in response to the step of comparing, moving each movable member through the increment for each determination in a group to which the movable member is related when the specimen has reacted, the moving of the movable member both exposing the representation for the condition when the specimen has reacted and forming a score value for each determination, the movable member being moved sequentially until a total group score value for each group is obtained, the representation of each movable member after moving enabling the representation to be checked against the predetermined indicia and different predetermined indicia of the test; and d. assembling the score values of all groups into a final value which is distinctive for each different combination of group score values, the final value being indicative of the indentification of the unknown substance.

20. In a method in accordance with claim 19 in which the step of arranging the tests into at least one group comprises arranging the tests into groups containing equal numbers of determinations.

21. In a method in accordance with claim 20 in which each group includes five determinations.

22. In a method in accordance with claim 19 in which the step of assembling the numerical score values of all groups into a final value comprises the step of placing the numerical score values of all groups into different positions in accordance with a predetermined format. The format presenting the final value.

23. In a method in accordance with claim 22 in which the step of positioning the numerical group score values of all groups into a predetermined format comprises arranging the numerical group score values into a sequence in correspondence to the predetermined order of the groups.

* * * * *

UNITED STATES PATENT AND TRADEMARK OFFICE
CERTIFICATE OF CORRECTION

PATENT NO. : 3936356
DATED : February 3, 1976
INVENTOR(S) : Pierre R. Janin

It is certified that error appears in the above–identified patent and that said Letters Patent are hereby corrected as shown below:

Col. 7, line 52, after "each" insert --test--.

Col. 15, line 38, "ag2" should be --agar--.

Col. 16, the table at line 35 should read --49. Tryptophane-
    peptane    red ring    yellow ring--.

Col. 18, line 52, "31 4" should read --  -4 --.

Col. 20, line 36, "audification" should read --acidification--.

Signed and Sealed this twenty-ninth Day of June 1976

[SEAL]

Attest:

RUTH C. MASON
Attesting Officer

C. MARSHALL DANN
Commissioner of Patents and Trademarks